(12) United States Patent  
Yamada et al.

(10) Patent No.: US 8,624,231 B2
(45) Date of Patent: Jan. 7, 2014

(54) BENZOPYRENE COMPOUND AND ORGANIC LIGHT-EMITTING ELEMENT CONTAINING THE SAME

(75) Inventors: Naoki Yamada, Inagi (JP); Yosuke Nishide, Kawasaki (JP); Maki Okajima, Kawasaki (JP); Tetsuo Takahashi, Tokyo (JP); Jun Kamatani, Tokyo (JP); Akihito Saitoh, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 313 days.

(21) Appl. No.: 13/076,194

(22) Filed: Mar. 30, 2011

(65) Prior Publication Data

US 2011/0240976 A1 Oct. 6, 2011

(30) Foreign Application Priority Data

Mar. 31, 2010 (JP) ................................. 2010-082818

(51) Int. Cl.
*H01L 35/24* (2006.01)
*H01L 51/00* (2006.01)

(52) U.S. Cl.
USPC ..................................... 257/40; 257/E51.026

(58) Field of Classification Search
USPC .......................................... 257/40, E51.026
See application file for complete search history.

(56) References Cited

U.S. PATENT DOCUMENTS 6,930,134 B2 * 8/2005 Suzuki et al. ................... 522/25
2008/0007160 A1 * 1/2008 Sado et al. ................... 313/504

FOREIGN PATENT DOCUMENTS

JP 05032966 A 2/1993
JP 09241629 A 9/1997

* cited by examiner

*Primary Examiner* — Howard Weiss
(74) *Attorney, Agent, or Firm* — Canon USA Inc. IP Division

(57) ABSTRACT

A benzopyrene compound represented by a general formula [1] below,

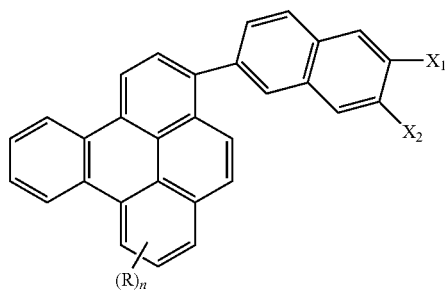

where one of $X_1$ and $X_2$ represents a substituted or unsubstituted aryl group; another one of $X_1$ and $X_2$ represents a hydrogen atom; R represents an alkyl group; and n represents 0 or 1.

7 Claims, 1 Drawing Sheet

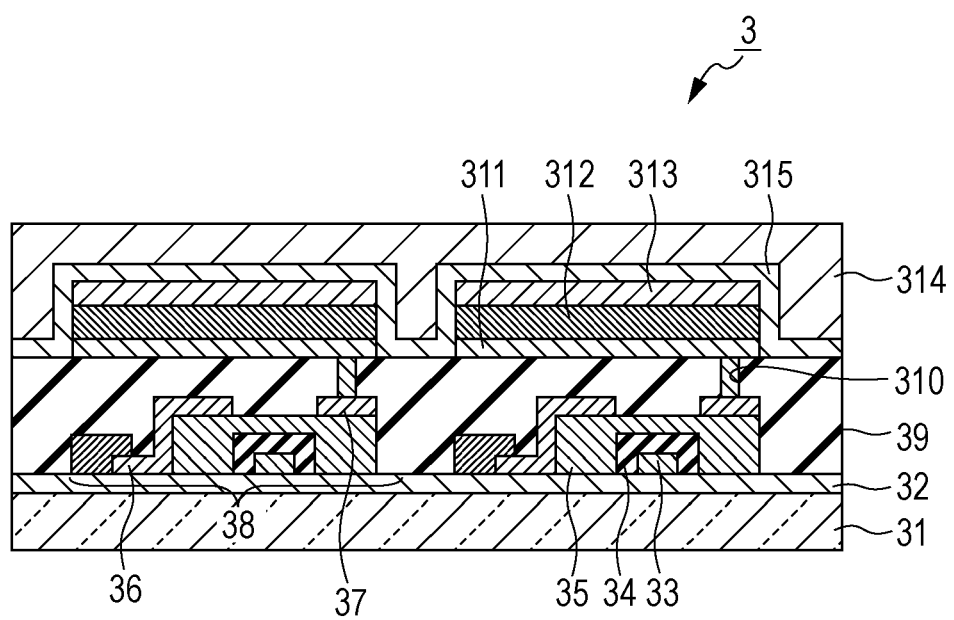

BENZOPYRENE COMPOUND AND ORGANIC LIGHT-EMITTING ELEMENT CONTAINING THE SAME

BACKGROUND OF THE INVENTION

1. Field of the Invention

The present invention relates to a novel benzopyrene compound and an organic light-emitting element containing such a novel benzopyrene compound.

2. Description of the Related Art

Recently, organic light-emitting elements have been remarkably developed.

However, organic light-emitting elements that output light at a higher luminous intensity or have a higher conversion efficiency are being required. In addition, organic light-emitting elements still have many problems in terms of durability against, for example, aging caused by use for a long period of time or degradation caused by oxygen, moisture, or the like. When organic light-emitting elements are used for full-color displays or the like, the organic light-emitting elements are required to have a high color purity and emit blue light at a high efficiency. However, current organic light-emitting elements do not satisfy these requirements. On the other hand, organic light-emitting elements that particularly have a high color purity, a high light-emitting efficiency, and a high durability and materials for forming such organic light-emitting elements have been demanded.

Then, attempts have been made to use organic compounds having a benzo[e]pyrene skeleton for light-emitting elements and structural formulae (A) and (B) below have been disclosed (Japanese Patent Laid-Open Nos. 09-241629 and 05-032966, respectively). However, in view of light-emitting hue, light-emitting efficiency, luminous intensity, and durability, further improvements are required.

Structural formula (A)

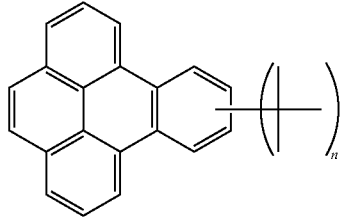

where n represents an integer of 0 to 12.

Structural formula (B)

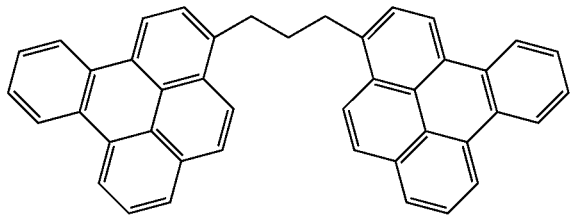

The organic compounds described in the above-described patent documents and organic light-emitting elements containing the organic compounds need to be improved for practical use.

Specifically, to achieve the practical use of such organic light-emitting elements, the organic light-emitting elements need to output light at a higher luminous intensity or have a higher conversion efficiency. Furthermore, the organic light-emitting elements need to be improved in terms of durability against, for example, aging caused by use for a long period of time or degradation caused by oxygen, moisture, or the like.

In addition, when organic light-emitting elements are used for full-color displays or the like, the organic light-emitting elements are required to have a high color purity and emit blue light at a high efficiency. However, current organic light-emitting elements do not satisfy these requirements.

Accordingly, in particular, organic light-emitting elements having a high drive voltage, a high light-emitting efficiency, and a high durability, and materials for forming such organic light-emitting elements have been demanded.

SUMMARY OF THE INVENTION

Embodiments of the present invention have been accomplished to solve the above-described problems. Specifically, aspects of the present invention provide a novel compound having a wide band gap of 2.90 eV or more and 3.15 eV or less.

The inventors of the present invention have thoroughly studied and, as a result, the inventors have accomplished the present invention. Aspects of the present invention provide a benzopyrene compound represented by a general formula [1] below,

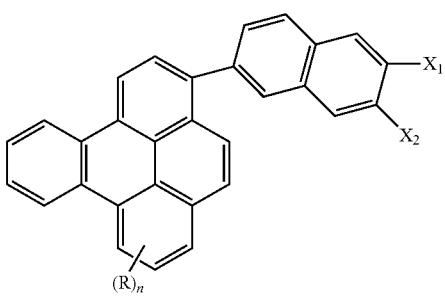

[1]

where one of $X_1$ and $X_2$ represents a substituted or unsubstituted aryl group; another one of $X_1$ and $X_2$ represents a hydrogen atom; R represents an alkyl group; and n represents 0 or 1.

Further features of the present invention will become apparent from the following description of exemplary embodiments with reference to the attached drawing.

BRIEF DESCRIPTION OF THE DRAWINGS

FIGURE is a schematic sectional view illustrating organic light-emitting elements and switching elements connected to the organic light-emitting elements.

DESCRIPTION OF THE EMBODIMENTS

A benzopyrene compound according to an embodiment of the present invention is represented by a general formula [1] below,

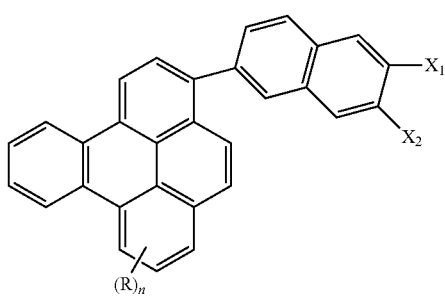

[1]

where one of $X_1$ and $X_2$ represents a substituted or unsubstituted aryl group, another one of $X_1$ and $X_2$ represents a hydrogen atom, R represents an alkyl group, and n represents 0 or 1.

Such an aryl group in the general formula [1] will be described. Examples of the aryl group include a phenyl group, a naphthyl group, a pentalenyl group, an anthryl group, a pyrenyl group, an indacenyl group, an acenaphthenyl group, a phenanthryl group, a phenalenyl group, a fluoranthenyl group, a benzofluoranthenyl group, an acephenanthryl group, an aceanthryl group, a triphenylenyl group, a chrysenyl group, a naphthacenyl group, a perylenyl group, a pentacenyl group, and a fluorenyl group. However, the aryl group is not restricted to these examples.

Examples of a substituent of such an aryl group include alkyl groups such as a methyl group, an ethyl group, and a propyl group; aralkyl groups such as a benzyl group and a phenethyl group; aryl groups such as a phenyl group and a biphenyl group; heterocyclic groups such as a thienyl group, a pyrrolyl group, and a pyridyl group; amino groups such as a dimethylamino group, a diethylamino group, a dibenzylamino group, diphenylamino group, a ditolylamino group, and a dianisolylamino group; alkoxyl groups such as a methoxyl group, an ethoxyl group, a propoxyl group, and a phenoxyl group; a cyano group; a nitro group; and halogen atoms such as fluorine and chlorine. However, the substituent is not restricted to these examples.

Such a benzopyrene compound has a wide band gap of 2.90 eV or more and 3.15 eV or less.

A compound represented by the general formula [1] has a structure in which the benzo[e]pyrene skeleton is substituted with a 1-naphthyl group and this naphthyl group is substituted with a fused polycyclic compound.

Benzo[e]pyrene, which has a band gap of 3.30 eV, is not suitable as a light-emitting material (having a band gap of 2.90 eV or more and 3.15 eV or less) for organic light-emitting elements because use of benzo[e]pyrene results in, for example, an increase in the drive voltage of organic light-emitting elements.

Compounds having a structure in which an alkyl group is bonded to benzo[e]pyrene have the same conjugation length as unsubstituted benzo[e]pyrene and hence probably have a band gap of about 3.30 eV. Similarly, compounds having a structure in which a phenyl group is bonded to benzo[e]pyrene probably have a large band gap and use of such a compound results in a high drive voltage.

In an embodiment of the present invention, by bonding a naphthyl group to benzo[e]pyrene, the band gap of the benzo[e]pyrene can be adjusted to a band gap suitable as a material for organic light-emitting elements and the drive voltage of organic light-emitting elements can be reduced.

The naphthyl group of a compound according to an embodiment of the present invention may be positioned at any substitution position of the benzo[e]pyrene skeleton of the compound. However, to effectively narrow the band gap, substitution with a naphthyl group is conducted at a position where the HOMO-LUMO are highly occupied by electrons. Thus, the substitution position may be a position corresponding to a substituent Y in a formula below. The following formula is a general formula illustrating a benzo[e]pyrene skeleton and the substituent Y at a specific position.

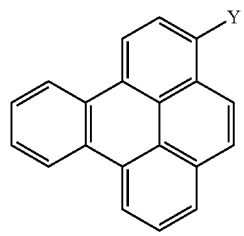

Table 1 below shows the band gaps of spin-coated films (serving as examples of solid films) formed of compounds according to embodiments of the present invention and benzo[e]pyrene.

TABLE 1

| Compound | Band gap eV |
|---|---|
| Benzo[e]pyrene | 3.30 |
| A-1 | 2.99 |
| A-2 | 3.10 |
| A-4 | 3.08 |

Such a band gap can be measured with a visible-ultraviolet absorption spectrum. Herein, a 0.1% chloroform solution of each compound was applied to a glass substrate by a spin coat method to form a spin-coated film and the band gap of the compound was measured with the absorption edge of the film. In this measurement, a spectrophotometer U-3010 manufactured by Hitachi, Ltd. was used.

Substitution of the benzo[e]pyrene moiety in the general formula [1] with an alkyl group serving as a steric hindrance group reduces the occurrence of intermolecular stacking. Accordingly, when a compound according to an embodiment of the present invention is used for an organic light-emitting element, a stable amorphous film of the compound can be formed in which the occurrence of intermolecular stacking is reduced and hence crystallization is suppressed. Such an alkyl group for reducing the occurrence of intermolecular stacking may be any alkyl group. However, in particular, a bulky alkyl group such as a tertiary butyl group or an isopropyl group is effectively used.

Whichever position of the benzo[e]pyrene moiety is used for substitution with such an alkyl group, the effect of reducing the occurrence of intermolecular stacking is probably similarly provided.

A compound according to an embodiment of the present invention may have a structure in which the naphthyl group is substituted with a fused polycyclic group. Materials for organic light-emitting elements need to form stable amorphous films. A compound according to an embodiment of the present invention has a structure in which the naphthyl group is substituted with a fused polycyclic compound. As a result, the glass transition temperature of the compound is increased and stable amorphous films can be formed from the compound, which contributes to an increase in the life of organic light-emitting elements.

The substitution position of the naphthyl group with such a fused polycyclic group may be any position. However, since the planarity of the entire molecular structure needs to be enhanced for the purpose of enhancing the mobility of electrons or holes, the substitution position may correspond to X1 or X2 in the general formula [1]. When a substitution position other than X1 and X2 is employed, peri-position repulsion in the naphthyl group or steric repulsion due to the benzo[e]pyrenyl group causes a loss of the planarity between the naphthyl group and the fused polycyclic group.

Examples of a fused polycyclic compound according to an embodiment of the present invention are illustrated below in the form of structural formulae.

A-1
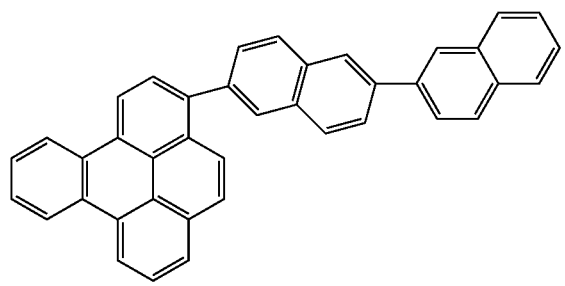

A-2
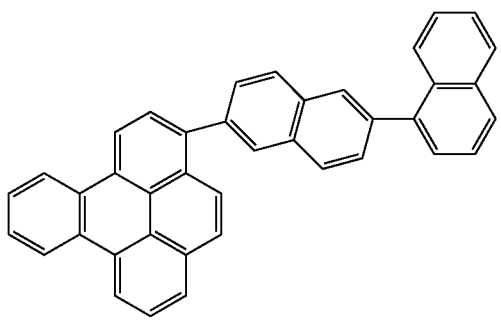

A-3
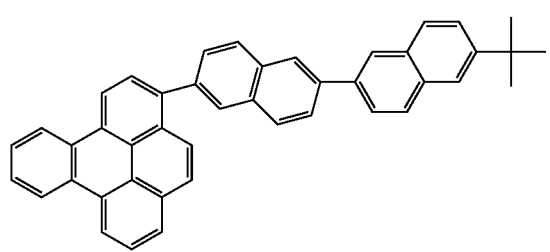

A-4
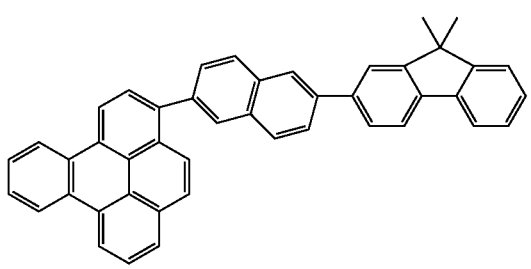

A-5
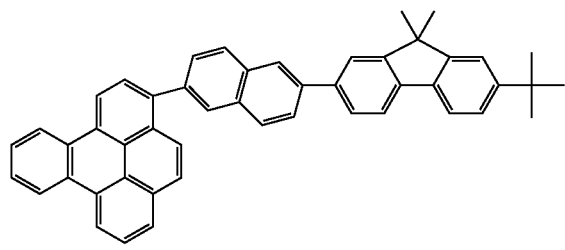

A-6
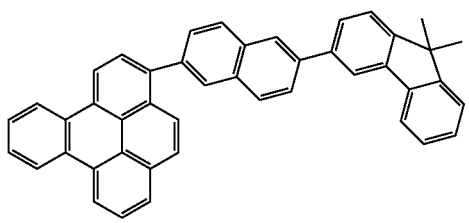

A-7
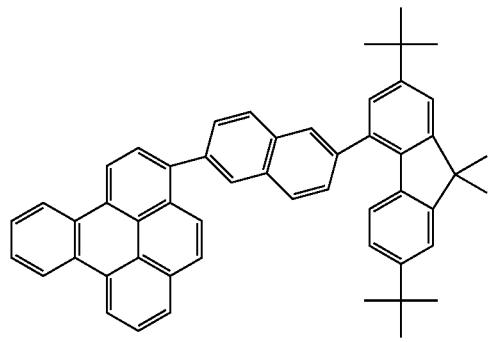

A-8
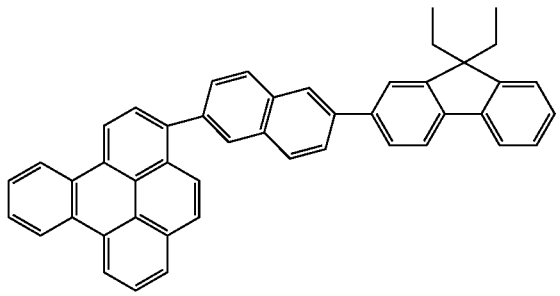

-continued
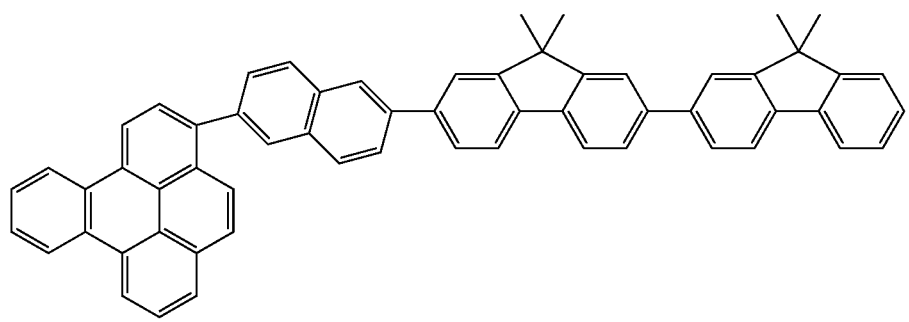
A-9
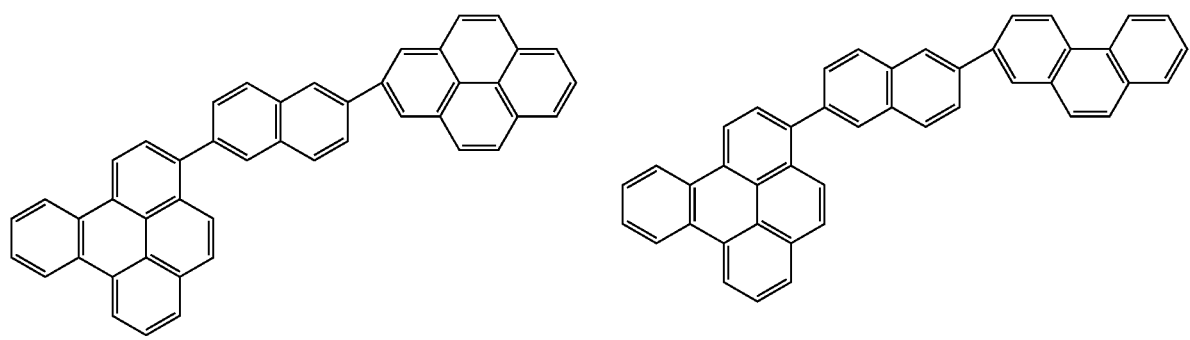
A-10    A-11
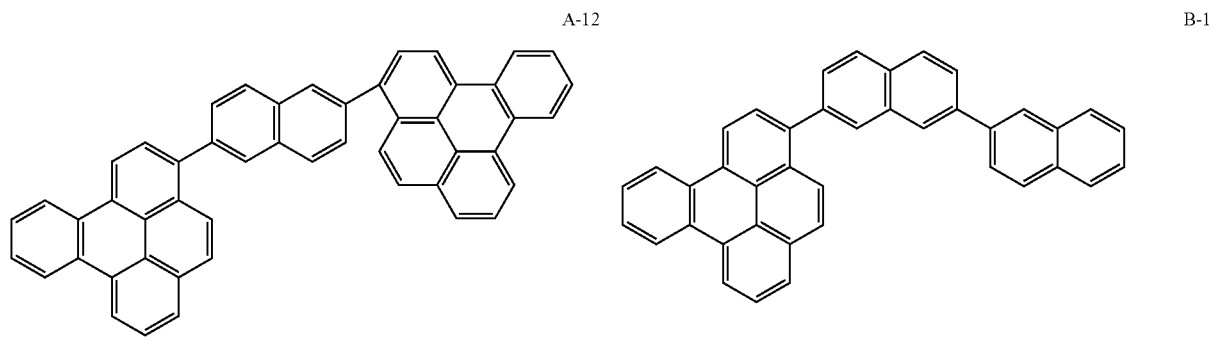
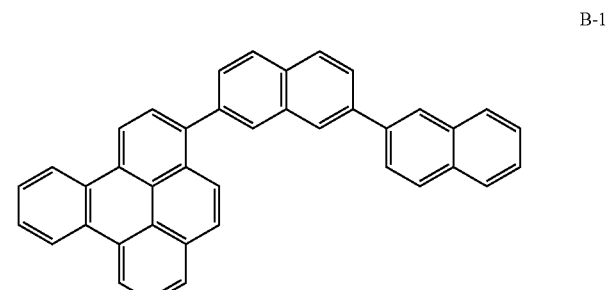
A-12    B-1
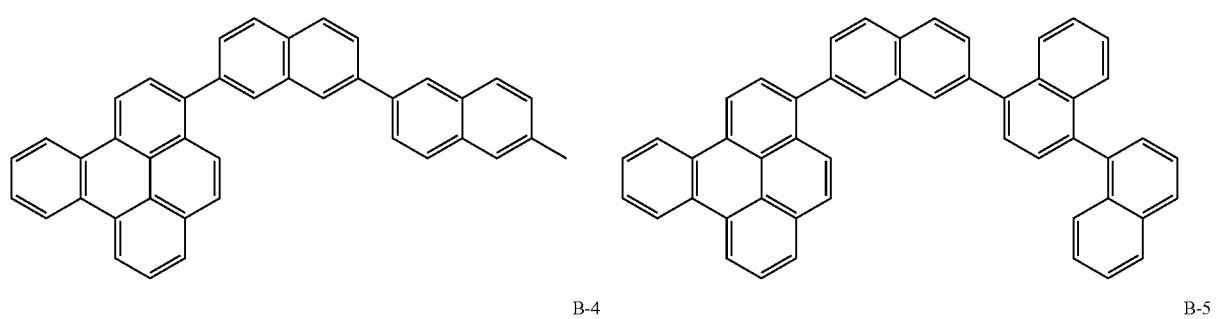
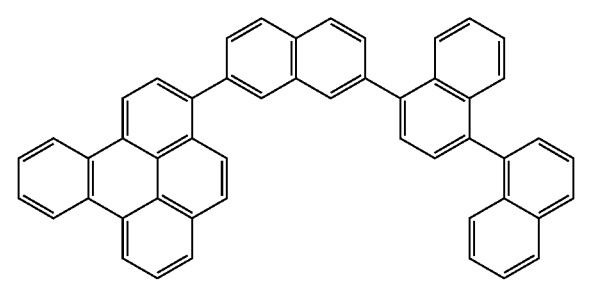
B-2    B-3
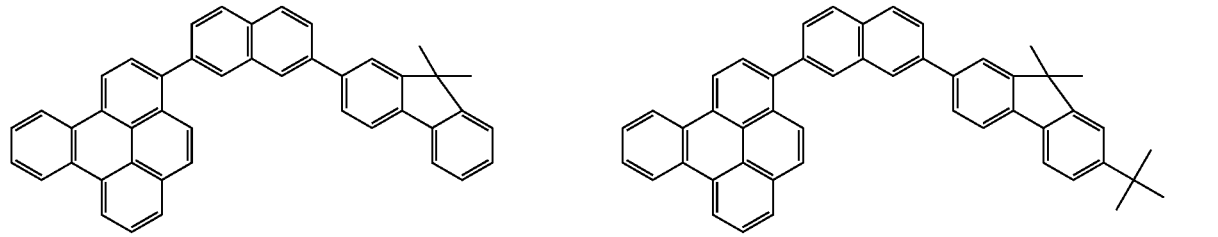
B-4    B-5

-continued
B-6
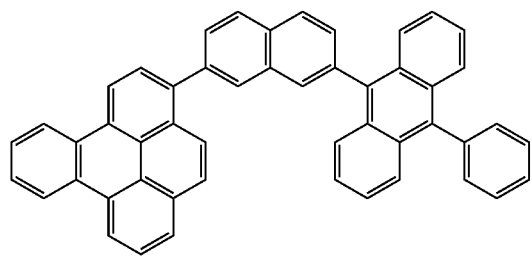
B-7
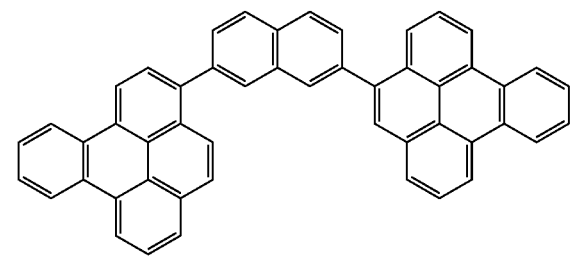
B-8
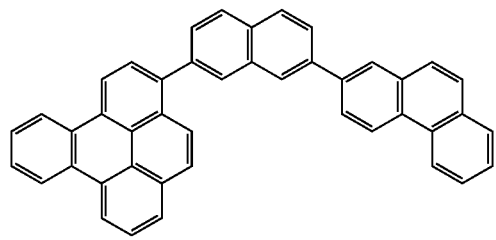
B-9
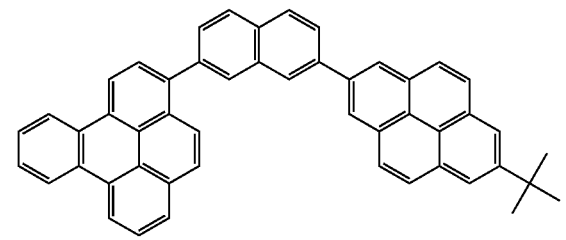
C-1
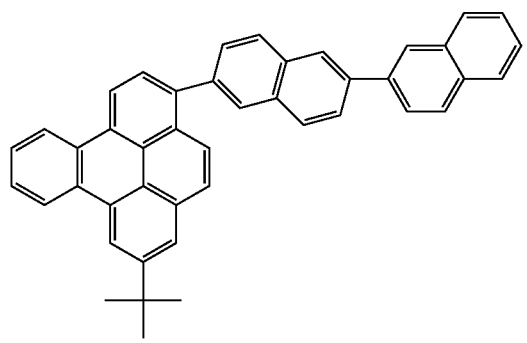
C-2
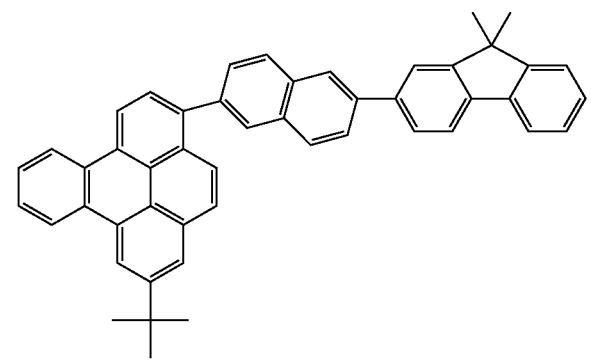
C-3
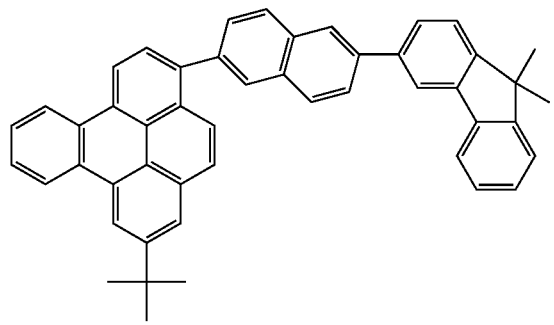
C-4
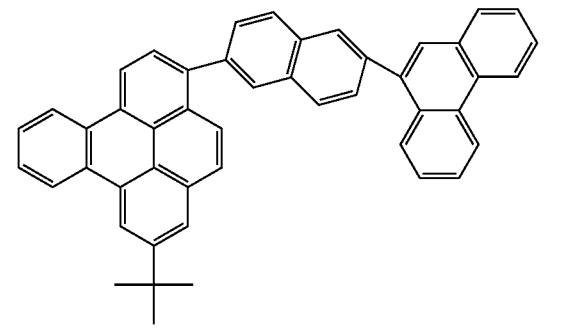
C-5
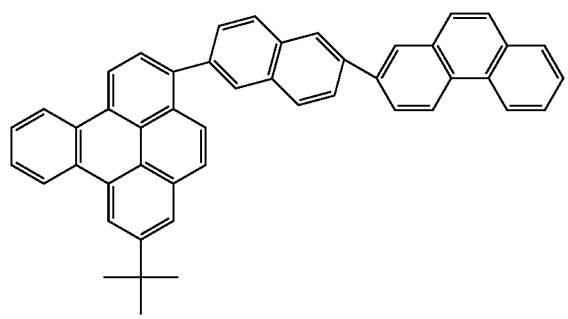
C-6
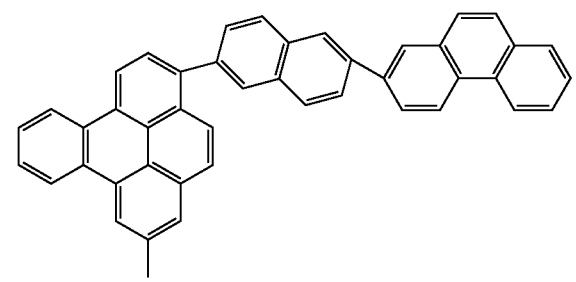

-continued

C-7

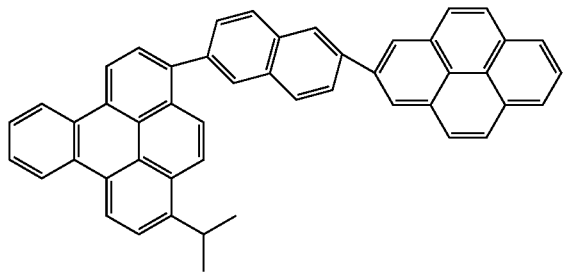

C-8

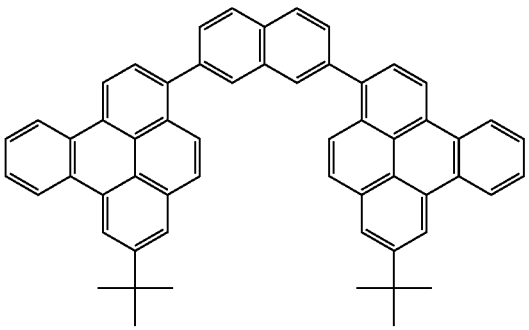

C-9

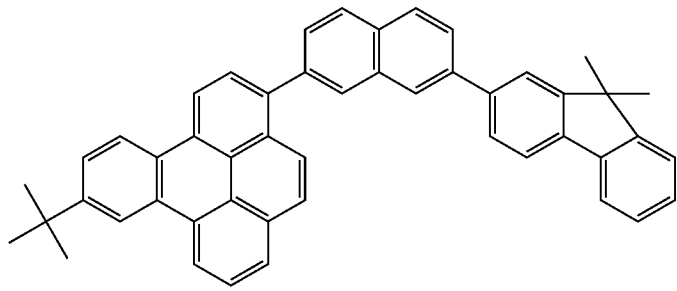

Of these, some benzopyrene compounds will be described in Examples below.

The compounds described in Examples, which are compounds represented by the general formula [1], can be summarized as compounds represented by a general formula [2] below.

That is, the compounds are benzopyrene compounds represented by the following general formula [2],

[2]

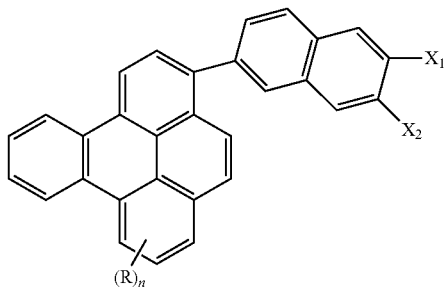

where one of $X_1$ and $X_2$ represents a hydrogen atom; another one of $X_1$ and $X_2$ represents a substituted or unsubstituted aryl group; the aryl group is any one of a naphthyl group, a fluorenyl group, a pyrenyl group, a benzopyrenyl group, an anthryl group, and a phenanthryl group; the naphthyl group, the fluorenyl group, the pyrenyl group, the benzopyrenyl group, the anthryl group, and the phenanthryl group may have a methyl group, a tertiary butyl group, a naphthyl group, a phenyl group, or an isopropyl group; R represents a tertiary butyl group; and n represents 0 or 1.

In such a case, a benzopyrene compound according to an embodiment of the present invention has an advantage below in addition to the advantage of having a wide band gap of 2.90 eV or more and 3.15 eV or less.

The benzopyrene compound can have a band gap suitable as a material for organic light-emitting elements. When the benzopyrene compound is used as a host material of luminescent sublayers of organic light-emitting elements or used to form electron transport layers of organic light-emitting elements, the drive voltage of such organic light-emitting elements is reduced. A naphthyl group, a fluorenyl group, a pyrenyl group, a benzopyrenyl group, an anthryl group, and a phenanthryl group, which may be employed as X1 and X2, are appropriate substituents that provide compounds according to embodiments of the present invention having a band gap of 2.90 eV or more and 3.15 eV or less. These substituents have a high planarity and hence compounds having a high mobility are provided.

According to one aspect, X1 represents any one of an unsubstituted naphthyl group, a naphthyl group having a methyl group or a tertiary butyl group, an unsubstituted fluorenyl group, and a fluorenyl group having a methyl group or a tertiary butyl group; and X2 represents a hydrogen atom. In such a case, the drive voltage can be further reduced.

Compounds represented by the general formula [1] can be used as materials for organic light-emitting elements. In particular, compounds represented by the general formula [1] can be used to form a hole transport layer, an electron transport layer, and a luminescent sublayer. In this case, organic light-emitting elements having a high light-emitting efficiency and a long life can be provided.

The term "luminescent sublayer" denotes a layer that emits light. An organic light-emitting element according to an embodiment of the present invention may include a functional layer in addition to such a luminescent sublayer. In this case, the organic light-emitting element has a structure in which layers including the luminescent sublayer and the functional layer are stacked. The layer configuration of such an organic light-emitting element will be described below.

An organic compound layer serving as a luminescent sublayer contains a compound represented by the general formula [1]. The luminescent sublayer may be formed of a compound represented by the general formula [1] only. Alternatively, a compound represented by the general formula [1] may be used as a guest material of the luminescent sublayer.

Herein, the term "guest material" denotes a material that substantially determines the emission color of an organic light-emitting element and emits light. The term "host material" denotes a material having a higher compositional ratio than such a guest material.

In an organic luminescent sublayer, a host material has a high compositional ratio and a guest material has a low compositional ratio. Herein, such a compositional ratio is represented in weight percent in which the total weight of all the components constituting the organic compound layer serves the denominator.

When a compound represented by the general formula [1] is used as a guest material of an organic luminescent sublayer, the content thereof may be 0.1 wt % or more and 30 wt % or less with respect to the total weight of the luminescent sublayer. According to one aspect, to suppress concentration quenching, the content of such a compound is 0.1 wt % or more and 15 wt % or less. Such a range may also be provided when an organic compound layer is composed of a host material and a guest material only.

In an organic compound layer, a guest material may be uniformly contained in the entirety of the organic compound layer or may be contained so as to form a concentration gradient. Alternatively, an organic compound layer may have a region containing a guest material and another region not containing the guest material. A benzopyrene compound represented by the general formula [1] may be used to form an electron transport layer.

Hereinafter, an organic light-emitting element according to an embodiment of the present invention will be described in detail. An organic light-emitting element according to an embodiment of the present invention includes a pair of electrodes constituted by an anode and a cathode, and one or more layers that contain an organic compound and are disposed between the pair of electrodes. At least one layer among the one or more layers that contain an organic compound contains at least one compound represented by the general formula [1].

In addition to the organic compound layer, another compound layer may be disposed between the pair of electrodes facing each other. Two or more compound layers including the organic compound layer may be disposed between the pair of electrodes. In such a case, the organic light-emitting element is referred to as a multilayer organic light-emitting element. Hereinafter, the first to fifth examples of such a multilayer organic light-emitting element will be described.

The first example of a multilayer organic light-emitting element has a configuration in which an anode, a luminescent sublayer, and a cathode are sequentially disposed on a substrate. Such an organic light-emitting element is advantageous in the case where a single organic compound having a hole transport capability, an electron transport capability, and a light-emitting capability is used and in the case where compounds having such capabilities are mixed.

The second example of a multilayer organic light-emitting element has a configuration in which an anode, a hole transport layer, an electron transport layer, and a cathode are sequentially disposed on a substrate. Such an organic light-emitting element is advantageous in the case where a light-emitting material having a hole transport capability or an electron transport capability or both capabilities is used to form a layer and, the light-emitting material is combined with a hole transport material without a light-emitting capability or an electron transport material without a light-emitting capability. In this case, a hole transport layer or an electron transport layer serves as a luminescent sublayer.

The third example of a multilayer organic light-emitting element has a configuration in which an anode, a hole transport layer, a luminescent sublayer, an electron transport layer, and a cathode are sequentially disposed on a substrate. In this configuration, the carrier transport function and the light-emitting function are separated. Compounds having a hole transport capability, an electron transport capability, and a light-emitting capability can be appropriately combined. Accordingly, the degree of freedom with which materials are selected is considerably enhanced and various compounds having different light-emitting wavelengths can be used. Thus, various light-emitting hues can be provided. Furthermore, carriers or excitons can be effectively confined within the central luminescent sublayer to thereby enhance a light-emitting efficiency.

The fourth example of a multilayer organic light-emitting element has a configuration in which an anode, a hole injection layer, a hole transport layer, a luminescent sublayer, an electron transport layer, and a cathode are sequentially disposed on a substrate. This configuration enhances the adhesion between the anode and the hole transport layer or enhances hole injection properties, which effectively results in low-voltage driving.

The fifth example of a multilayer organic light-emitting element has a configuration in which an anode, a hole transport layer, a luminescent sublayer, a hole-exciton blocking layer, an electron transport layer, and a cathode are sequentially disposed on a substrate. In this configuration, the hole-exciton blocking layer that blocks passing of holes or excitons toward the cathode is disposed between the luminescent sublayer and the electron transport layer. In this configuration, by forming the hole-exciton blocking layer with a compound having a very high ionization potential, the light-emitting efficiency is effectively enhanced.

However, the first to fifth examples show merely basic element configurations and the configuration of an organic light-emitting element including a compound according to an embodiment of the present invention is not restricted to these configurations. Various layer configurations may be employed: for example, an insulating layer is disposed at the interface between an electrode and an organic layer; a bonding layer or an interference layer is disposed; or an electron transport layer or a hole transport layer is constituted by two layers having different ionization potentials.

A compound according to an embodiment of the present invention may be used as a host material of a luminescent sublayer. However, a compound according to an embodiment of the present invention may be used to form a layer other than a luminescent sublayer and an electron transport layer, that is, any one of a hole injection layer, a hole transport layer, a hole-exciton blocking layer, and an electron injection layer.

Optionally, in addition to a compound according to an embodiment of the present invention, an existing compound such as a low molecular weight or high molecular weight hole transporting compound, a light-emitting compound, or an electron transporting compound can also be used.

As a hole injection/transport material, a material having a high hole mobility may be used so that holes can be readily injected from an anode and the injected holes can be transported to a luminescent sublayer. Examples of a low molecular weight or high molecular weight hole injection/transport material include triarylamine derivatives, phenylenediamine derivatives, stilbene derivatives, phthalocyanine derivatives, porphyrin derivatives, poly(vinylcarbazole), poly(thiophene), and other conductive polymers. However, these examples are not limitative.

Examples of a host material mainly include fused cyclic compounds such as fluorene derivatives, naphthalene derivatives, anthracene derivatives, pyrene derivatives, carbazole derivatives, quinoxaline derivatives, and quinoline derivatives; organic aluminum complexes such as tris(8-quinolinolate) aluminum; organic zinc complexes; triphenylamine derivatives; polymer derivatives such as triphenylamine derivatives, poly(fluorene) derivatives, and poly(phenylene) derivatives. However, these examples are not limitative.

An electron injection/transport material can be freely selected from materials to which electrons are readily injected from a cathode and from which the injected electrons can be transported to a luminescent sublayer. An electron injection/transport material is selected in consideration of, for example, a balance relating to the hole mobility of a hole injection/transport material. Examples of a material having an electron injection/transport capability include oxadiazole derivatives, oxazole derivatives, pyrazine derivatives, triazole derivatives, triazine derivatives, quinoline derivatives, quinoxaline derivatives, phenanthroline derivatives, and organic aluminum complexes. However, these examples are not limitative.

An anode material may have a work function as high as possible. Examples of an anode material include elemental metals such as gold, platinum, silver, copper, nickel, palladium, cobalt, selenium, vanadium, and tungsten; alloys of such metals; metal oxides such as tin oxide, zinc oxide, indium oxide, indium tin oxide (ITO), and indium zinc oxide; and conductive polymers such as polyaniline, polypyrrole, and polythiophene. Such electrode materials may be used alone or in combination. An anode may have a monolayer structure or a multilayer structure.

On the other hand, a cathode material may have a low work function. Examples of a cathode material include alkali metals such as lithium; alkaline-earth metals such as calcium; elemental metals such as aluminum, titanium, manganese, silver, lead, and chromium; alloys of these elemental metals such as a magnesium-silver alloy, an aluminum-lithium alloy, and an aluminum-magnesium alloy; and metal oxides such as indium tin oxide (ITO). Such electrode materials may be used alone or in combination. A cathode may have a monolayer structure or a multilayer structure.

A substrate including an organic light-emitting element according to an embodiment of the present invention is not particularly restricted. For example, an opaque substrate such as a metal substrate or a ceramic substrate, or a transparent substrate such as a glass substrate, a quartz substrate, or a plastic-sheet substrate may be used. By combining a substrate and a color filter film, a fluorescent color conversion filter film, a dielectric reflection film, or the like, emitted color light can be controlled.

For the purpose of preventing a fabricated element from being in contact with oxygen, moisture, or the like, a protective layer or a sealing layer may be provided. Examples of such a protective layer include diamond thin films; inorganic material films such as metal oxide films and metal nitride films; polymer films such as fluorocarbon resin films, polyethylene films, silicone resin films, and polystyrene films; and photocurable resin films. Alternatively, a fabricated element may be covered with glass, a gas barrier film, a metal, or the like and may be packaged with an appropriate sealing resin.

In an organic light-emitting element according to an embodiment of the present invention, a layer containing an organic compound according to an embodiment of the present invention and a layer composed of another organic compound can be formed in the following manner. In general, a thin film is formed by a vacuum deposition method, an ionization deposition method, sputtering, a plasma deposition method, or an existing application method in which a solution prepared by dissolving an organic compound in a solvent is applied, such as spin coating, dipping, a casting method, a Langmuir-Blodgett (LB) method, or an inkjet method. Of these methods, when a vacuum deposition method, a solution application method, or the like is employed to form a layer, crystallization or the like is less likely to be caused and the layer is excellent in terms of stability over time. When such an application method is employed to form a film, the film may be composed of an organic compound and an appropriate binder resin.

Examples of such a binder resin include polyvinyl carbazole resins, polycarbonate resins, polyester resins, ABS resins, acrylic resins, polyimide resins, phenolic resins, epoxy resins, silicone resins, and urea resins. However, these examples are not limitative. Such a binder resin may be used alone in the form of a homopolymer or a copolymer, or in combination as a mixture of two or more thereof. Optionally, such a binder resin may be combined with an existing additive such as a plasticizer, an antioxidant, or an ultraviolet absorbing agent.

An organic light-emitting element according to an embodiment of the present invention can be applied to products that need to have a high energy efficiency or a high luminous intensity. Examples of such an application include display devices, lighting devices, light sources of printers, and backlights of liquid crystal display apparatuses.

Such display devices may be flat-panel displays that have a high energy efficiency, a high visibility, or a light weight. Such display devices may be image display devices of PCs, television receivers, advertising media, or the like. Alternatively, such display devices may be used for display sections of image capturing apparatuses such as digital still cameras or digital video cameras.

Alternatively, such display devices may be used for operation display sections of electrophotographic image forming apparatuses such as laser beam printers or copiers.

Such display devices may be used as light sources used in exposure of latent images on photo conductors of electrophotographic image forming apparatuses such as laser beam printers or copiers. A latent image can be formed by performing exposure on a photoconductor drum in a predetermined manner with arrays (for example, in the form of lines) of independently addressable organic light-emitting elements. By using an organic light-emitting element according to an embodiment of the present invention, spaces having been required to place a light source, a polygon mirror, various optical lenses, and the like can be saved.

By using an organic light-emitting element according to an embodiment of the present invention as a lighting device or a backlight, energy consumption can be reduced. An organic light-emitting element according to an embodiment of the present invention can be used as a planar light source.

By providing a color filter film, a fluorescent color conversion filter film, a dielectric reflection film, or the like on a substrate supporting organic light-emitting elements according to an embodiment of the present invention, emitted color light can be controlled. Switching between light emission and non-light emission can be controlled with a thin-film transistor (TFT) disposed on a substrate and connected to an organic light-emitting element. A plurality of organic light-emitting elements may be arranged in a matrix, that is, arranged within a plane and can be used as a lighting device.

Hereinafter, a display device including organic light-emitting elements according to an embodiment of the present invention will be described. FIGURE is a schematic sectional view of an image Display Device Including Organic Light-Emitting elements in a pixel section. FIGURE illustrates two organic light-emitting elements and two TFTs. One organic light-emitting element is connected to one TFT.

An image display device 3 includes TFT elements 38 serving as switching elements; a substrate 31, a vapor barrier film 32, gate electrodes 33, gate insulating films 34, semiconductor layers 35, drain electrodes 36, source electrodes 37, an insulating film 39, contact holes 310, anodes 311, organic layers 312, cathodes 313, a first protective layer 314, and a second protective layer 315.

The image display device 3 includes the vapor barrier film 32 on the substrate 31 composed of glass or the like. The vapor barrier film 32 protects components (TFTs or organic layers) formed thereon. A material for forming the vapor barrier film 32 is, for example, silicon oxide or a composite of silicon oxide and silicon nitride. The gate electrodes 33 are disposed on the vapor barrier film 32. The gate electrodes 33 can be formed by forming a film of a metal such as Cr by sputtering.

The gate insulating films 34 are disposed so as to cover the gate electrodes 33. The gate insulating films 34 are formed by forming a film of silicon oxide or the like by a plasma CVD method, a catalytic chemical vapor deposition method (cat-CVD method), or the like, and patterning the film. The semiconductor layers 35 are disposed so as to cover the gate insulating films 34 each disposed in regions corresponding to TFTs. The semiconductor layers 35 can be formed by forming a silicon film by a plasma CVD method or the like (optionally, the film is annealed at a temperature of, for example, 290° C. or more) and patterning the film in accordance with the shape of a circuit.

The drain electrode 36 and the source electrode 37 are disposed for each of the semiconductor layers 35. Thus, each TFT element 38 includes the gate electrode 33, the gate insulating film 34, the semiconductor layer 35, the drain electrode 36, and the source electrode 37. The insulating film 39 is disposed over the TFT elements 38. The contact holes (through holes) 310 are formed so as to extend through the insulating film 39. The anodes 311 composed of a metal for organic light-emitting elements and the source electrodes 37 are connected to each other through the contact holes 310.

Each organic layer 312 that has a multilayer structure including a luminescent sublayer or a monolayer structure of a luminescent sublayer and each cathode 313 are sequentially stacked on each anode 311 to constitute each organic light-emitting element.

To suppress degradation of the organic light-emitting elements, the first protective layer 314 or the second protective layer 315 may be provided. The switching elements are not particularly restricted and MIM elements other than the TFT elements may be employed.

The light-emitting elements may have a bottom-emission configuration in which light is extracted from the substrate side of the light-emitting elements, or a top-emission configuration in which light is extracted from a side of the light-emitting elements, the side being opposite the substrate side.

Hereinafter, aspects of the present invention will specifically be described with reference to Examples. However, the present invention is not restricted to these Examples.

Example 1

Synthesis of Exemplified Compound A-2

Exemplified compound A-2 was synthesized in accordance with the following scheme.

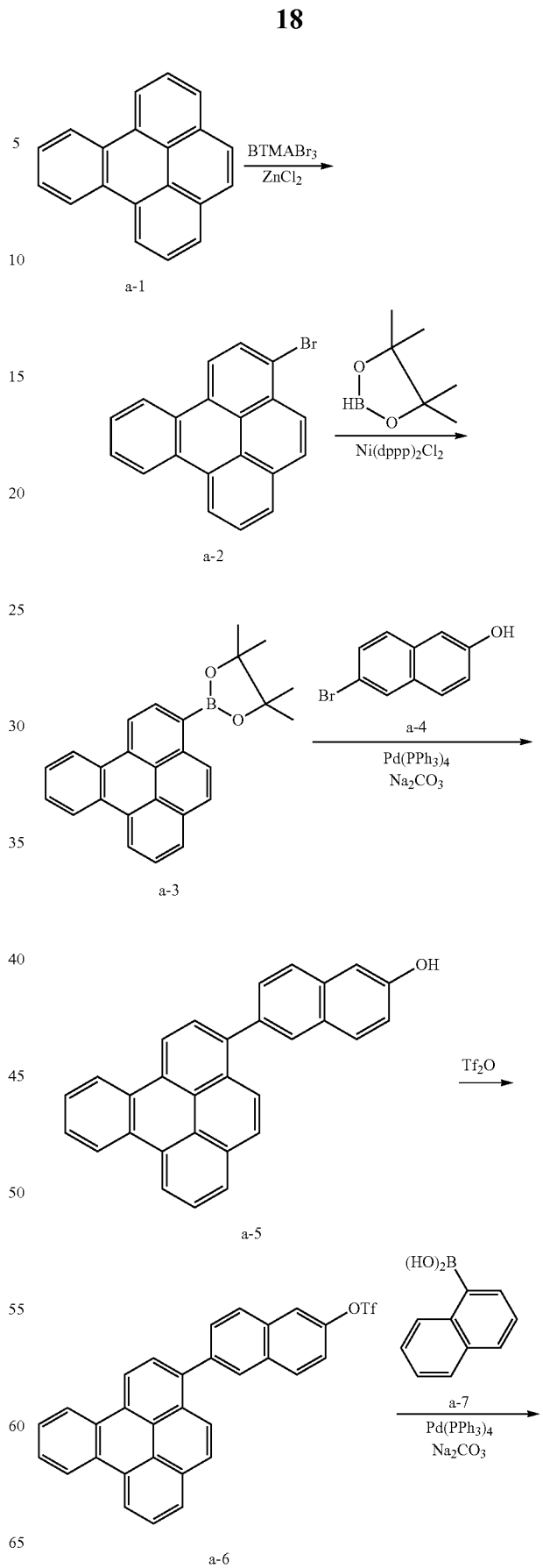

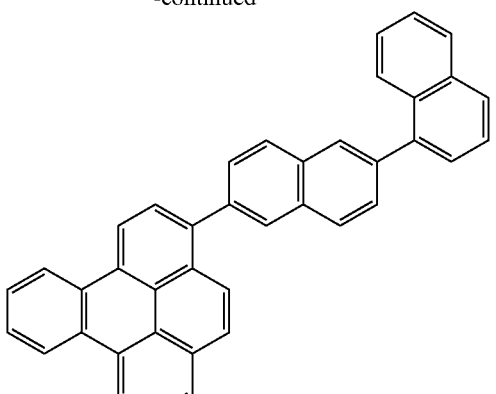

A-2

A 100 ml three-neck flask was charged with 0.900 g (3.57 mmol) of Compound a-1, 1.389 g (3.56 mmol) of benzyltrimethylammonium tribromide, 0.486 g (3.57 mmol) of zinc chloride, and 60 ml of chloroform. The resultant mixture was stirred for 3 hours at room temperature to cause a reaction. After the reaction, the resultant solution was mixed with 100 ml of water. The organic layer of the resultant solution was extracted with toluene, dried with anhydrous sodium sulfate, and subsequently purified with a silica gel column (developing solvent: toluene-heptane mixture) to give 0.963 g (yield: 96%) of Compound a-2 (white crystals).

b) Synthesis of Compound a-3

A 100 ml three-neck flask was charged with 0.900 g (3.43 mmol) of Compound a-2, 188 mg (0.343 mmol) of [1,1'-bis(diphenylphosphino)propane]dichloronickel, 0.99 ml (6.85 mmol) of 4,4,5,5-tetramethyl-1,3,2-dioxaborolan, 30 ml of toluene, and 5 ml of triethylamine. The resultant mixture was brought to a temperature of 90° C. in a nitrogen atmosphere and stirred for 6 hours to cause a reaction. After the reaction, the resultant solution was mixed with 50 ml of water. After the reaction, the organic layer of the resultant solution was extracted with toluene, dried with anhydrous sodium sulfate, and subsequently purified with a silica gel column (developing solvent: toluene-heptane mixture) to give 1.10 g (yield: 84.7%) of Compound a-3 (white crystals).

c) Synthesis of Compound a-5

A 100 ml three-neck flask was charged with 0.624 g (2.80 mmol) of Compound a-4, 1.10 g (2.91 mmol) of Compound a-3, 20 ml of toluene, and 10 ml of ethanol. While the resultant solution was stirred at room temperature in a nitrogen atmosphere, an aqueous solution prepared by mixing 10 g of sodium carbonate and 20 ml of water was dropped thereinto, and 0.161 mg of tetrakis(triphenylphosphine)palladium(0) was subsequently added thereto. The resultant solution was brought to a temperature of 77° C. and stirred for 5 hours to cause a reaction. After the reaction, the organic layer of the resultant solution was extracted with toluene, dried with anhydrous sodium sulfate, and subsequently purified with a silica gel column (developing solvent: toluene-heptane mixture) to give 0.94 g (yield: 85%) of Compound a-5 (white crystals).

d) Synthesis of Compound a-6

A 200 ml three-neck flask was charged with 0.94 g (2.38 mmol) of Compound a-5 and 50 ml of anhydrous pyridine. While the resultant mixture was stirred in a nitrogen atmosphere under ice cooling, 0.56 ml (4.47 mmol) of trifluoromethanesulfonic anhydride (Tf2O) was slowly dropped thereinto and stirred for an hour. The resultant reaction solution was stirred at room temperature for 2 hours. After the reaction, the reaction solution was mixed with 50 ml of water. The organic layer of the resultant solution was extracted with toluene, dried with anhydrous sodium sulfate, and subsequently purified with a silica gel column (developing solvent: toluene-heptane mixture) to give 1.09 g (yield: 87%) of Compound a-6 (white crystals).

e) Synthesis of Exemplified compound A-2

A 100 ml three-neck flask was charged with 0.50 g (0.95 mmol) of Compound a-6, 0.180 g (1.04 mmol) of Compound a-7, 1.06 g (10.0 mmol) of sodium carbonate, 30 ml of toluene, 10 ml of ethanol, and 20 ml of water. While the resultant solution was stirred at room temperature in a nitrogen atmosphere, 57.8 mg of tetrakis(triphenylphosphine)palladium(0) was added thereto. The resultant solution was brought to a temperature of 80° C. and stirred for 5 hours to cause a reaction. After the reaction, the organic layer of the resultant solution was extracted with toluene, dried with anhydrous sodium sulfate, and subsequently purified with a silica gel column (developing solvent: toluene-heptane mixture) to give 0.360 g (yield: 75%) of Exemplified compound A-2 (yellow-white crystals). This compound was analyzed by mass spectrometry and was found to have M+ at 504, which characterizes Exemplified compound A-2.

The structure of Exemplified compound A-2 was analyzed by 1HNMR measurement. $^1$H NMR (CDCl$_3$, 400 MHz) δ (ppm): 9.01 (d, 1H), 8.95 (d, 1H), 8.93-8.87 (m, 1H), 8.24-7.92 (m, 12H), 7.84 (d, 1H), 7.79-7.77 (m, 2H), 7.74 (d, 2H), 7.62-7.59 (m, 2H), 7.55-7.48 (m, 4H) The band gap of a spin-coated film of Exemplified compound A-2 was found to be 3.10 eV.

Such a band gap can be measured with a visible-ultraviolet absorption spectrum. Herein, a 0.1% chloroform solution of each compound was applied to a glass substrate by a spin coat method to form a spin-coated film and the band gap of the film was measured with the absorption edge of the film. In this measurement, a spectrophotometer U-3010 manufactured by Hitachi, Ltd. was used.

Example 2

Synthesis of Exemplified Compound A-4

Exemplified compound A-4 was synthesized in accordance with the following scheme.

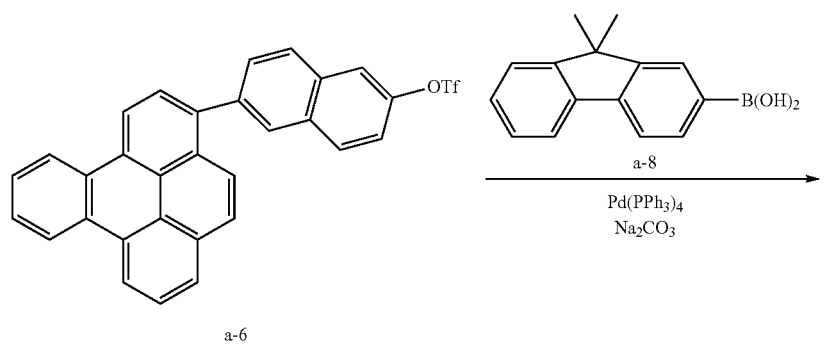

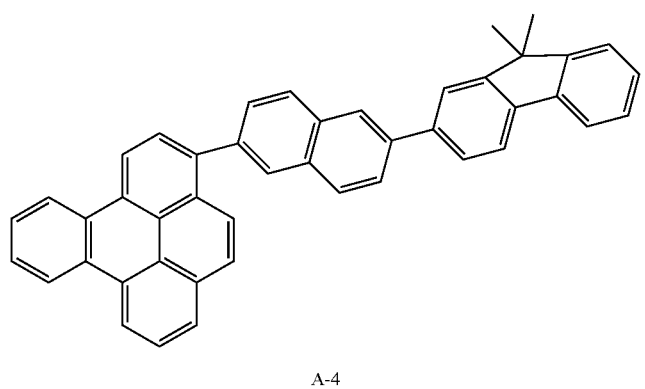

A 100 ml three-neck flask was charged with 0.50 g (0.95 mmol) of Compound a-6, 0.248 g (1.04 mmol) of Compound a-8, 1.06 g (10.0 mmol) of sodium carbonate, 30 ml of toluene, 10 ml of ethanol, and 20 ml of water. While the resultant solution was stirred at room temperature in a nitrogen atmosphere, 57.8 mg of tetrakis(triphenylphosphine)palladium(0) was added thereto. The resultant solution was brought to a temperature of 80° C. and stirred for 5 hours to cause a reaction. After the reaction, the organic layer of the resultant solution was extracted with toluene, dried with anhydrous sodium sulfate, and subsequently purified with a silica gel column (developing solvent: toluene-heptane mixture) to give 0.423 g (yield: 78%) of Exemplified compound A-4 (white-yellow crystals). This compound was analyzed by mass spectrometry and was found to have M+ at 570, which characterizes Exemplified compound A-4.

The structure of Exemplified compound A-4 was analyzed by 1HNMR measurement. $^1$H NMR (CDCl$_3$, 600 MHz) δ (ppm): 9.01 (d, 1H), 8.96 (d, 1H), 8.88-8.94 (m, 2H), 8.25 (s, 1H), 8.23 (d, 1H), 8.19 (d, 1H), 8.15 (s, 2H), 8.12 (d, 1H), 8.07 (t, 1H), 8.06 (d, 1H), 8.02 (d, 1H), 7.93 (dd, 1H), 7.87 (t, 1H), 7.85 (s, 1H), 7.83 (dd, 1H), 7.78-7.81 (m, 4H), 7.50 (d, 1H), 7.35-7.40 (m, 2H), 1.61 (s, 6H). The band gap of a spin-coated film of Exemplified compound A-4 was found to be 3.08 eV. The same measurement method as in Example 1 was used.

Example 3

Synthesis of Exemplified Compound A-1

Exemplified compound A-1 was synthesized in accordance with the following scheme.

-continued

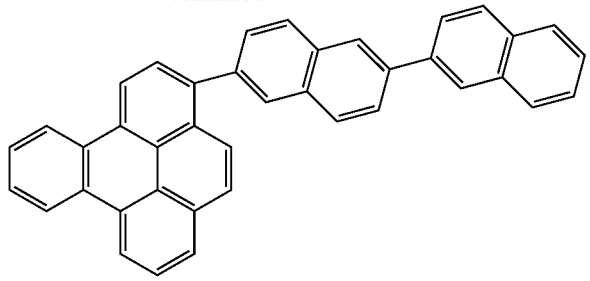

A-1

A 100 ml three-neck flask was charged with 0.50 g (0.95 mmol) of Compound a-6, 0.180 g (1.04 mmol) of Compound a-9, 1.06 g (10.0 mmol) of sodium carbonate, 30 ml of toluene, 10 ml of ethanol, and 20 ml of water. While the resultant solution was stirred at room temperature in a nitrogen atmosphere, 57.8 mg of tetrakis(triphenylphosphine)palladium(0) was added thereto. The resultant solution was brought to a temperature of 80° C. and stirred for 5 hours to cause a reaction. After the reaction, the organic layer of the resultant solution was extracted with toluene, dried with anhydrous sodium sulfate, and subsequently purified with a silica gel column (developing solvent: toluene-heptane mixture) to give 0.335 g (yield: 70%) of Exemplified compound A-1 (white-yellow crystals). This compound was analyzed by mass spectrometry and was found to have M+ at 504, which characterizes Exemplified compound A-1. The band gap of a spin-coated film of Exemplified compound A-1 was found to be 2.99 eV. The same measurement method as in Example 1 was used.

Example 4

Synthesis of Exemplified Compound A-5

Exemplified compound A-5 was synthesized in accordance with the following scheme.

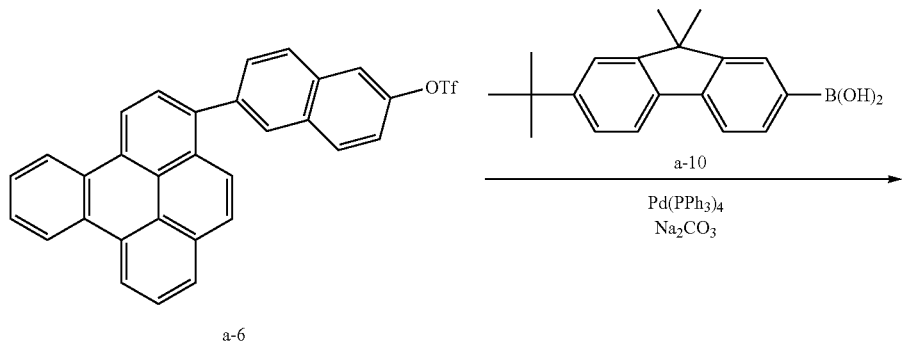

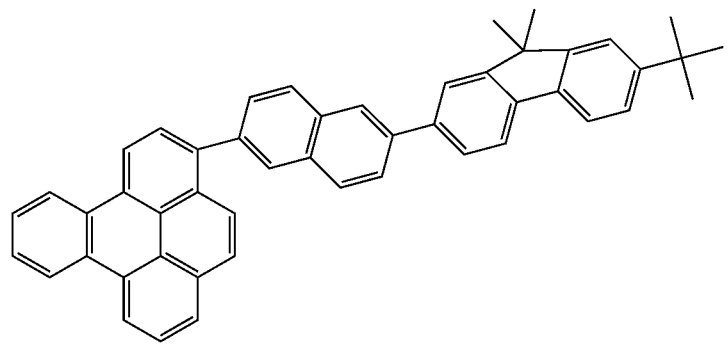

A-5

A 100 ml three-neck flask was charged with 0.50 g (0.95 mmol) of Compound a-6, 0.306 g (1.04 mmol) of Compound a-10, 1.06 g (10.0 mmol) of sodium carbonate, 30 ml of toluene, 10 ml of ethanol, and 20 ml of water. While the resultant solution was stirred at room temperature in a nitrogen atmosphere, 57.8 mg of tetrakis(triphenylphosphine)palladium(0) was added thereto. The resultant solution was brought to a temperature of 80° C. and stirred for 5 hours to cause a reaction. After the reaction, the organic layer of the resultant solution was extracted with toluene, dried with anhydrous sodium sulfate, and subsequently purified with a silica gel column (developing solvent: toluene-heptane mixture) to give 0.417 g (yield: 70%) of Exemplified compound A-5 (white-yellow crystals). This compound was analyzed by mass spectrometry and was found to have M+ at 626, which characterizes Exemplified compound A-5.

Example 5

Synthesis of Exemplified Compound A-11

Exemplified compound A-11 was synthesized in accordance with the following scheme.

A 100 ml three-neck flask was charged with 0.50 g (0.95 mmol) of Compound a-6, 0.231 g (1.04 mmol) of Compound a-11, 1.06 g (10.0 mmol) of sodium carbonate, 30 ml of toluene, 10 ml of ethanol, and 20 ml of water. While the resultant solution was stirred at room temperature in a nitrogen atmosphere, 57.8 mg of tetrakis(triphenylphosphine)palladium(0) was added thereto. The resultant solution was brought to a temperature of 80° C. and stirred for 5 hours to cause a reaction. After the reaction, the organic layer of the resultant solution was extracted with toluene, dried with anhydrous sodium sulfate, and subsequently purified with a silica gel column (developing solvent: toluene-heptane mixture) to give 0.400 g (yield: 76%) of Exemplified compound A-11 (white-yellow crystals). This compound was analyzed by mass spectrometry and was found to have M+ at 554, which characterizes Exemplified compound A-11.

Example 6

Synthesis of Exemplified Compound C-1

Exemplified compound C-1 was synthesized in accordance with the following scheme. Compound a-12 was synthesized in the same manner as in Example 1 except that Compound a-1 was replaced with Compound a-13.

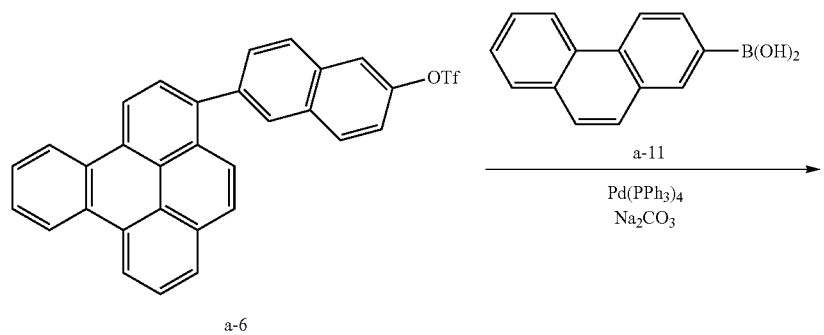

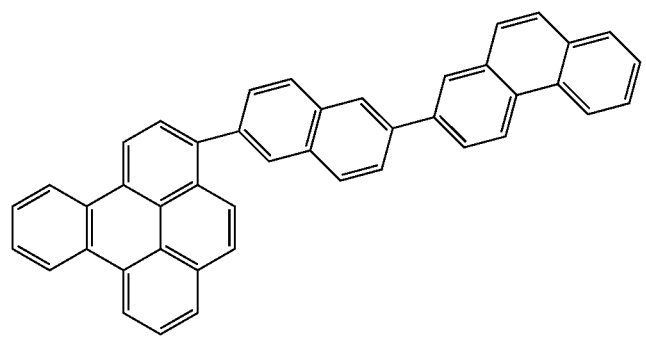

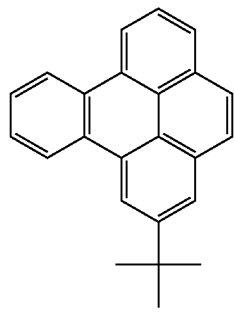

a-13

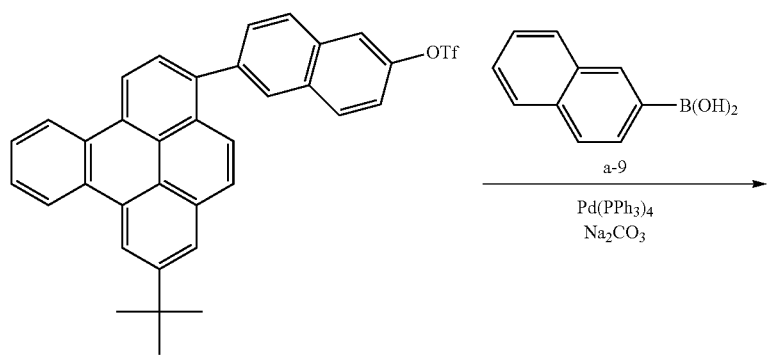

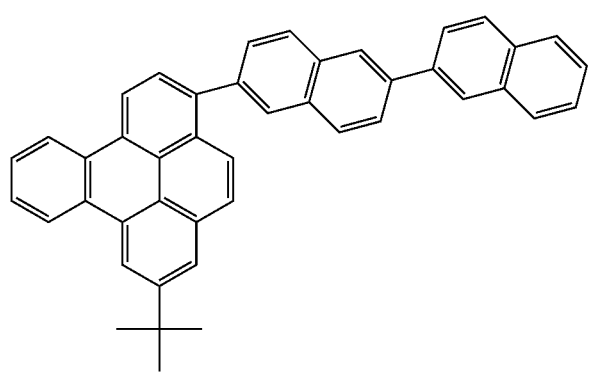

C-1

A 100 ml three-neck flask was charged with 0.50 g (0.95 mmol) of Compound a-12, 0.181 g (1.05 mmol) of Compound a-9, 1.06 g (10.0 mmol) of sodium carbonate, 30 ml of toluene, 10 ml of ethanol, and 20 ml of water. While the resultant solution was stirred at room temperature in a nitrogen atmosphere, 57.8 mg of tetrakis(triphenylphosphine)palladium(0) was added thereto. The resultant solution was brought to a temperature of 80° C. and stirred for 5 hours to cause a reaction. After the reaction, the organic layer of the resultant solution was extracted with toluene, dried with anhydrous sodium sulfate, and subsequently purified with a silica gel column (developing solvent: toluene-heptane mixture) to give 0.373 g (yield: 70%) of Exemplified compound C-1 (white-yellow crystals). This compound was analyzed by mass spectrometry and was found to have M+ at 560, which characterizes Exemplified compound C-1.

Example 7

Synthesis of Exemplified Compound C-2

Exemplified compound C-2 was synthesized in accordance with the following scheme.

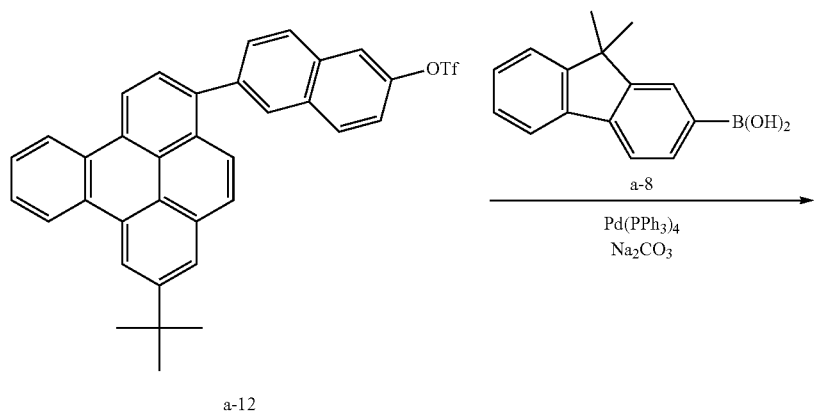

a-12

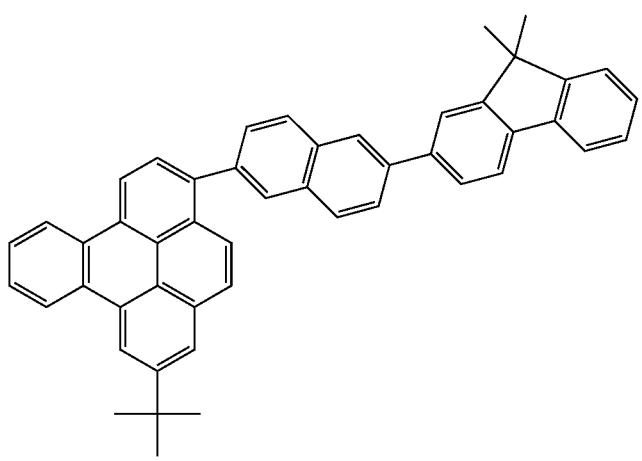

C-2

A 100 ml three-neck flask was charged with 0.50 g (0.95 mmol) of Compound a-12, 0.181 g (1.05 mmol) of Compound a-8, 1.06 g (10.0 mmol) of sodium carbonate, 30 ml of toluene, 10 ml of ethanol, and 20 ml of water. While the resultant solution was stirred at room temperature in a nitrogen atmosphere, 57.8 mg of tetrakis(triphenylphosphine)palladium(0) was added thereto. The resultant solution was brought to a temperature of 80° C. and stirred for 5 hours to cause a reaction. After the reaction, the organic layer of the resultant solution was extracted with toluene, dried with anhydrous sodium sulfate, and subsequently purified with a silica gel column (developing solvent: toluene-heptane mixture) to give 0.435 g (yield: 73%) of Exemplified compound C-2 (white-yellow crystals). This compound was analyzed by mass spectrometry and was found to have M+ at 626, which characterizes Exemplified compound C-2.

Exemplified compounds B-4, B-7, and B-9 can be synthesized in the same manner as in Example 1 except that Compounds a-4 and a-7 are replaced with the following naphthalene derivative and pinacol-boron compounds shown in Table 2 below.

TABLE 2

| Exemplified compound No. | Naphthalene derivative | Pinacol-boron compounds |
|---|---|---|
| B-4 | | |

TABLE 2-continued

| Exemplified compound No. | Naphthalene derivative | Pinacol-boron compounds |
|---|---|---|
| B-7 | 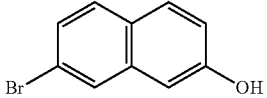 | 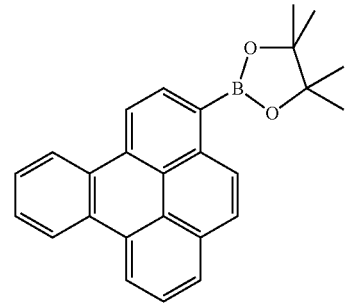 [SMILES: CC1(C)OB(c2ccc3c4ccccc4c4cccc5ccc2c3c54)OC1(C)C] |
| B-9 | 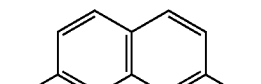 | 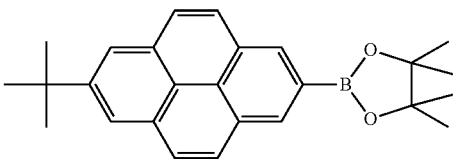 [SMILES: CC(C)(C)c1cc2ccc3cc(B4OC(C)(C)C(C)(C)O4)cc4ccc(c1)c2c34] |

Example 8

Fabrication of Element

A film that was composed of indium tin oxide (ITO) and served as an anode was formed on a glass substrate by a sputtering method so as to have a thickness of 120 nm. This substrate was subjected to ultrasonic cleaning with acetone and then with isopropyl alcohol (IPA). Then, the substrate was cleaned by being boiled with IPA and subsequently dried. This substrate was then subjected to UV/ozone cleaning. The resultant substrate was used as a transparent conductive support substrate. A film of Compound d-1 below was formed with a chloroform solution of Compound d-1 on the transparent conductive support substrate by a spin coat method so as to have a thickness of 11 nm. Thus, a hole injection layer was formed.

Furthermore, organic layers and electrode layers listed below were successively formed by vacuum deposition with resistance heating in a vacuum chamber at 10-5 Pa. Thus, an electroluminescent (EL) element was fabricated.

Hole transport layer (15 nm): Compound d-2
Luminescent sublayer (30 nm): Compound d-3 (concentration: 5 wt %) and Exemplified compound A-4 (concentration: 95 wt %)
Electron transport layer (30 nm): Compound d-4
First metal electrode layer (0.5 nm): LiF
Second metal electrode layer (150 nm): Al Compound d-1

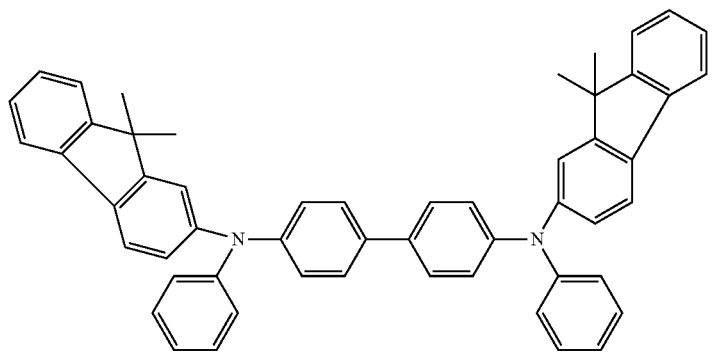

-continued

Compound d-2

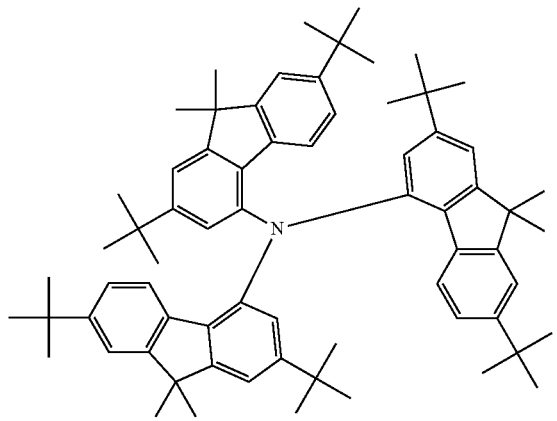

Compound d-3

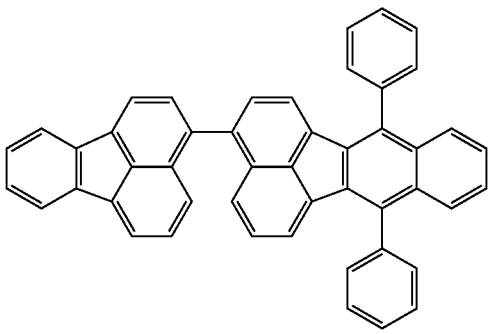

Compound d-4

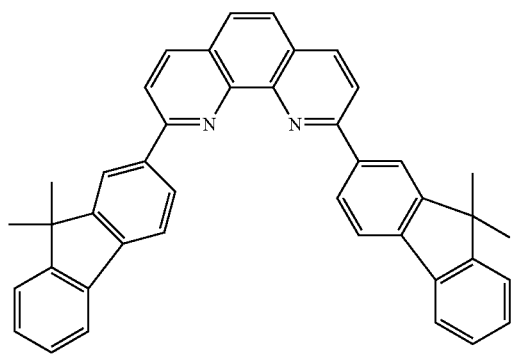

A voltage of 5.0 V was applied to the EL element in Example 8 and, as a result, blue-light emission having a luminous intensity of 2084 cd/m² and a CIE chromaticity (0.15, 0.27) was observed.

A voltage was continuously applied for 100 hours to the EL element while a current density of 100 mA/cm² was maintained in a nitrogen atmosphere. As a result, a luminance degradation percentage of the EL element after the lapse of 100 hours with respect to the initial luminous intensity was a small value of 30% or less.

Example 9

Fabrication of Element

A film that was composed of indium tin oxide (ITO) and served as an anode was formed on a glass substrate by a sputtering method so as to have a thickness of 120 nm. This substrate was subjected to ultrasonic cleaning with acetone and then with isopropyl alcohol (IPA). Then, the substrate was cleaned by being boiled with IPA and subsequently dried. This substrate was then subjected to UV/ozone cleaning. The resultant substrate was used as a transparent conductive support substrate. A film of Compound d-1 was formed with a chloroform solution of Compound d-1 on the transparent conductive support substrate by a spin coat method so as to have a thickness of 11 nm. Thus, a hole injection layer was formed.

Furthermore, organic layers and electrode layers listed below were successively formed by vacuum deposition with resistance heating in a vacuum chamber at 10-5 Pa. Thus, an electroluminescent (EL) element was fabricated.

Hole transport layer (15 nm): Compound d-2
Luminescent sublayer (30 nm): Compound d-3 (concentration: 5 wt %) and Compound d-6 (concentration: 95 wt %)
Electron transport layer (30 nm): Compound A-2
First metal electrode layer (0.5 nm): LiF
Second metal electrode layer (150 nm): Al Compound d-6

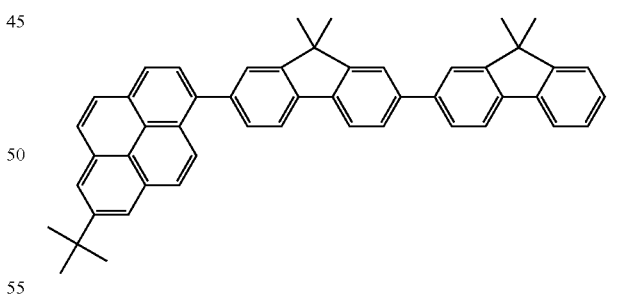

A voltage of 5.0 V was applied to the EL element in Example 9 and, as a result, blue-light emission having a luminous intensity of 1834 cd/m² and a CIE chromaticity (0.16, 0.27) was observed.

A voltage was continuously applied for 100 hours to the EL element while a current density of 100 mA/cm2 was maintained in a nitrogen atmosphere. As a result, a luminance degradation percentage of the EL element after the lapse of 100 hours with respect to the initial luminous intensity was a small value of 15% or less. As has been described so far with reference to embodiments and Examples, aspects of the present invention can provide a novel benzopyrene compound. Specifically, aspects of the present invention can provide a benzopyrene compound represented by the general formula [1]. Such a compound has a wide band gap of 2.90 eV or more and 3.15 eV or less.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-082818, filed Mar. 31, 2010 which is hereby incorporated by reference herein in its entirety.

What is claimed is:

1. A benzopyrene compound represented by a general formula [1] below,

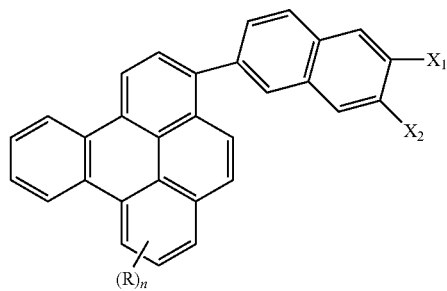

[1]

where one of $X_1$ and $X_2$ represents a substituted or unsubstituted aryl group; another one of $X_1$ and $X_2$ represents a hydrogen atom; R represents an alkyl group; and n represents 0 or 1.

2. The benzopyrene compound according to claim 1, wherein $X_1$ represents the substituted or unsubstituted aryl group, and $X_2$ represents the hydrogen atom.

3. The benzopyrene compound according to claim 2, wherein $X_1$ represents a substituted or unsubstituted naphthyl group, fluorenyl group, benzopyrenyl group, or phenanthryl group.

4. An organic light-emitting element comprising:
a pair of electrodes facing each other; and
an organic compound layer that contains an organic compound and is disposed between the pair of electrodes,
wherein the organic compound includes the benzopyrene compound according to claim 1.

5. The organic light-emitting element according to claim 4, wherein the organic compound layer as a luminescent layer.

6. The organic light-emitting element according to claim 5, wherein the luminescent layer has the organic compound as a host material and the other organic compound as a guest material which emits light.

7. An image display device comprising:
a plurality of pixels,
wherein each of the plurality of pixels includes the organic light-emitting element according to claim 4 and a switching element connected to the organic light-emitting element.

* * * * *